(12) United States Patent
Casavant et al.

(10) Patent No.: US 7,130,685 B2
(45) Date of Patent: Oct. 31, 2006

(54) METHOD TO PREVENT PACEMAKER INDUCED NON-REENTRANT VA SYNCHRONY USING ADAPTIVE ATRIAL PACING OUTPUT

(75) Inventors: David A. Casavant, Reading, MA (US); Michael O. Sweeney, Brookline, MA (US); Robert A. Betzold, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 555 days.

(21) Appl. No.: 10/458,617

(22) Filed: Jun. 10, 2003

(65) Prior Publication Data

US 2004/0034390 A1  Feb. 19, 2004

Related U.S. Application Data

(60) Provisional application No. 60/387,979, filed on Jun. 10, 2002.

(51) Int. Cl.
*A61N 1/18* (2006.01)

(52) U.S. Cl. .......................................... 607/9; 607/119

(58) Field of Classification Search .................... 607/9, 607/11, 14, 25, 28
See application file for complete search history.

(56) References Cited

U.S. PATENT DOCUMENTS

| | | | |
|---|---|---|---|
| 4,505,276 A * | 3/1985 | Markowitz et al. | 600/510 |
| 4,557,266 A | 12/1985 | Schober | |
| 5,097,832 A * | 3/1992 | Buchanan | 607/14 |
| 5,273,035 A | 12/1993 | Markowitz et al. | |
| 5,374,280 A | 12/1994 | den Dulk | |
| 5,514,164 A | 5/1996 | Mann et al. | |
| 6,263,244 B1 | 7/2001 | Mann et al. | |
| 6,295,471 B1 * | 9/2001 | Bornzin et al. | 607/28 |
| 6,311,088 B1 * | 10/2001 | Betzold et al. | 607/14 |
| 6,477,419 B1 * | 11/2002 | Levine et al. | 607/14 |
| 6,625,489 B1 | 9/2003 | Sheth et al. | |

FOREIGN PATENT DOCUMENTS

WO   WO 93/14816   8/1993

OTHER PUBLICATIONS

Barold, S.S. "Pacemaker induced repetitive nonreentrant ventricular synchrony: initiation and termination by ventricular extrasystole", *Pacing Clin Electrophysiol*, 1997, 20 (4 Pt 1):989-92.

Barold S.S., Levine P.A., Isaeff D.M., et al., "Case Report: complex arrhythmia induced by noncompetitive atrial pacing algorithm of DDDR pacemaker", *J Interv Card Electrophysiol*, 2001, 5(4):431-4.

(Continued)

*Primary Examiner*—Robert E. Pezzuto
*Assistant Examiner*—Brian T. Gedeon
(74) *Attorney, Agent, or Firm*—Paul H. McDowall; Girma Wolde-Michael (57) ABSTRACT

The present invention is directed to the problem of preventing episodes of "AV Desynchronization Arrhythmia" (AVDA), a dual-chamber pacing behavior that is initiated by a PVC or other ventricular event that is not closely preceded by an atrial depolarization event. If the initiating PVC creates retrograde conduction resulting in an atrial refractory-sensed event, and should the succeeding AP fail to capture due to pacing within the atrial refractory period (ARP) a repetitive AVDA sequence ($AP_{ineffectual}$-VP-$AR_{refractory}$) can persist for an extended period of time and symptoms of pacemaker syndrome can occur. After AVDA detection, the following may occur: delivered atrial pacing (AP) energy may be (dynamically) increased, a atrial pacing (AP) delay interval may be implemented, a mode-switch may be executed, a patient notification process may begin, a histogram may be recorded or processed, and/or a combination thereof may be used in response the detected AVDA sequence.

24 Claims, 4 Drawing Sheets

OTHER PUBLICATIONS

Barold S. S. and Levine P.A., "Pacemaker repetitive nonreentrant ventriculoatrial synchronous rhythm. A Review", *J Interv Card Electrophysiol*, 2001, 5(1):45-58.

Durrer et al., "Total Excitation of the Isolated Human Heart", *Circulation*, Jun. 1970, vol. XLI, pp. 899-912.

* cited by examiner

METHOD TO PREVENT PACEMAKER INDUCED NON-REENTRANT VA SYNCHRONY USING ADAPTIVE ATRIAL PACING OUTPUT

CROSS REFERENCE TO RELATED APPLICATION

This patent disclosure claims the benefit of and incorporates the contents of prior provisional U.S. patent application Ser. No. 60/387,979 filed 10 Jun. 2002 and having the same title as the present non-provisional U.S. patent application.

FIELD OF THE INVENTION

The invention generally relates to the field of cardiac pacing; more particularly, to solving problems related to repetitive non-reentrant ventriculoatrial synchrony also known as "AV Desynchronization Arrhythmia" (AVDA). The AVDA sequence is a deleterious dual-chamber pacing behavior that is typically initiated by a premature ventricular contraction (PVC) or any premature ventricular event that is not closely preceded by an atrial depolarization. Once started, the AVDA pattern (i.e., $AP_{ineffectual}$-VP-$AR_{retrograde}$) typically persists until either VA conduction (i.e., retrograde conduction) fails or atrial capture is restored.

BACKGROUND OF THE INVENTION

Among patients having intact retrograde atrial-ventricular (AV) conduction, PVC or other ventricular events may cause retrograde atrial depolarizations that occur during the postventricular atrial refractory period (PVARP). These atrial depolarization events do not initiate a new AV interval but may render subsequent atrial pacing stimulus ineffectual (i.e., if provided during the physiologic refractory period of the atria). In older cardiac pacing regimens, this phenomenon was dealt with under the general rubric of pacemaker syndrome.

Currently, most cardiac pacing systems have automatic atrial tachyarrhythmia (AT) recognition. Shortly after AT detection such cardiac pacing systems change the operating mode (i.e., perform mode-switching) for example by performing so-called anti-tachycardia "overdrive" pacing (ATP) to halt the AT.

Various methods to safely restore AV synchrony following non-physiologic atrial events (e.g., retrograde p-waves) have been known and used in the art. One approach is to deliver an atrial pace stimulus following a fixed delay (e.g., 300 ms) to allow the refractory myocardial tissue to recover and thereby reduce the risk of provoking an AT by competitive atrial pacing. One pacemaker manufacturer refers to their technique as non-competitive atrial pacing (NCAP), another refers to their technique as atrial synchronization pacing (ASP). The NCAP approach may be adapted to avoid repetitive AVDA sequences by simply extending the NCAP delay following a refractory event (e.g., event deemed non-physiologic). Such an extended delay allows additional time for the excitable atrial myocardial tissue to fully recover. However, the downside to this approach is a significant disruption of the paced rhythm, especially during sensor-driven pacing.

Other intervals timed by a pacemaker or implantable pulse generator (IPG) include atrial and ventricular sense amplifier blanking periods following delivery of atrial and/or ventricular pacing pulses to disable atrial and ventricular amplifier sensing. In addition, sense amplifier refractory periods are timed- or switched-out following atrial and ventricular paced and sensed event signals. Such "refractory" A-sense and V-sense signals are selectively ignored or employed in a variety of ways; for example, to reset or extend time periods or to gather evidence that an arrhythmia is present, and the like. An atrial refractory period (ARP) extends for various time durations through the Sensed AV (SAV) delay or the Paced AV (PAV) delay.

In addition, a post-ventricular atrial refractory period (PVARP) begins at a V-PACE pulse or V-SENSE event. A-SENSE signals occurring during the PVARP are noted (e.g., counted as evidence that an arrhythmia is present) but do not start an AV interval. The rationale for this operation is that such events may be a retrograde atrial sensed (AR) event or an event that is part of an atrial tachycardia episode. In either case, it is not desirable to synchronize ventricular pacing to such events. The duration of the PVARP may be fixed by programming, extended after a PVC, or vary as a function of the pacing or heart rate, with the result that in many cases relatively long PVARPs are in effect at lower rates.

SUMMARY OF THE INVENTION

The inventors have discovered that during delivery of DDD/R and DDI/R pacing therapy—especially during sensor-driven pacing when the paced atrial rate is elevated or increasing due to sensor input (e.g., due to exertion by a patient)—the AVDA sequence can begin in response to an atrial refractory (AR) event caused by a retrograde-conducted ventricular depolarization (e.g., a PVC, paced ventricular depolarization, and the like). Since the AR event is not sensed, a scheduled but ineffectual atrial pacing (AP) stimulus delivered too soon after the AR event results in no atrial depolarization (due to the physiologic atrial refractory period). Subsequently, when a ventricular pacing (VP) stimulus is delivered it precipitates another ventricular depolarization that, in the presence of intact retrograde conduction, conducts to the atria and causes another retrograde atrial activation. This retrograde atrial activation typically occurs during an initial pre-programmed PVARP. Thus, an AVDA sequence can continue until either until retrograde conduction fails or atrial capture occurs during which time the pacemaker patient may be symptomatic (e.g., from loss of atrial contribution to stroke volume).

In addition, the inventors have discovered that AVDA appears to cause spurious mode-switching between various pacemaker pacing schemes. The requirements for such spurious mode-switching are (i) repetitive evoked retrograde atrial events occurring during the PVARP and (ii) such events used to increment a mode-switch counter.

In modern dual chamber pacemakers, the programmed initial PVARP may vary as a function of the heart rate or sensor rate. In the context of these types of pacemakers, the relatively long PVARPs that may be in effect at lower rates can, in the same fashion, result in a persistent AVDA pattern and/or spurious mode-switching as described above.

Multiple PVCs or PVC couplets that precipitate retrograde atrial depolarizations may also cause the AVDA pattern. Although the first PVC may trigger a long PVARP, e.g., 400 to 500 ms, the retrograde P-wave that falls into the refractory period fails to be officially sensed (or identified) as an atrial depolarization and thus, a next-scheduled but ineffectual atrial pacing (AP) stimulus is provided, then a ventricular pacing stimulus, then (again) another retrograde, refractory atrial event occurs, thus continuing the AVDA pattern. Therefore, a need exists in the art to detect and/or prevent repetitive AVDA sequences and to reestablish healthy cardiac rhythm without causing substantial delay or introducing a new cardiac rhythm to a pacemaker patient. Having discovered this deleterious AVDA sequence, the inventors set about (i) inventing methods for identifying repetitive AVDA sequences (i.e., $AP_{ineffectual}$-VP-$AR_{retrograde}$), (ii) halting any spurious pacemaker mode-switching behavior due to AVDA sequences, and (iii) restoring a desired pacing modality as quickly as possible for those patients who sustain such AVDA sequences, among other goals.

The present invention deals with problems related to AVDA: a dual-chamber pacing behavior that is typically initiated by a PVC or any ventricular event that is not closely preceded by an atrial depolarization.

The invention is also directed to the discovery (and beneficial avoidance) of harmful, spurious mode-switching in DDD/R pacing systems due to non-reentrant VA synchrony or AVDA.

According to the present invention, solutions to the problems related to spurious mode-switching include: using timing to safely restore AV synchrony following non-physiologic atrial events (e.g., retrograde p-waves) by delivering an atrial pace (AP) followed by a fixed delay to reduce the risk of provoking AT via "competitive pacing," and/or by increasing the AP energy delivered during the relative refractory period to simultaneously ensure capture and AT termination. In addition, apparatus and methods for avoiding the AVDA sequences are provided according to the present invention.

That is, in the broadest implementation of the teaching of the present invention, would not involve atrial output modulation (such as non-competitive atrial pacing or "NCAP," or atrial synchronization pacing or "ASP," both of which are described herein), but rather activate higher output pacing in the event that a pace is scheduled following a closely coupled atrial depolarization (i.e., occurring within about 300 ms).

Accordingly, a first aspect of the present invention involves modulating the atrial pacing output to a higher level following a closely coupled, non-physiologic, refractory-sensed atrial depolarization in order to increase the likelihood of capture and thereby prevent initiation of non-reentrant VA synchrony (AVDA).

The present invention is directed to the problem of reducing episodes of AVDA. If the initiating PVC creates retrograde conduction resulting in an atrial refractory-sensed event, and should the succeeding AP fail to capture because it occurs during the physiologic atrial refractory period (ARP) a repetitive pattern ($AP_{ineffectual}$-VP-$AR_{refractory}$) can persist for an extended period of time during which symptoms of pacemaker syndrome can occur.

The present invention also may be configured to provide an adaptive atrial pacing output during anti-bradycardia DDD/R operation in order to avoid atrial non-capture (and ensuing consequences) following intrinsic, non-physiologic atrial depolarizations.

The preceding summary and the specific embodiments described and depicted herein are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As every element, it may be replaced by any one of infinite equivalent alternatives, only some of which are disclosed in the specification. That is, although the invention is described with reference to particular embodiments, it will be understood to those skilled in the art that this embodiment is merely illustrative of the application of the principles of the invention.

The apparatus and methods of the present invention find utility in dual chamber devices having a pacing mode wherein at least one atria and one ventricular consistently receives pacing therapy at a rate determined least in part by an activity sensor, as is known in the art. For example, a dual chamber bradycardia pacing engine (e.g., DDD/R), a triple-chamber pacemaker used to provide pacing stimulus for patients suffering from heart failure (e.g., NYHA Class II–IV, CHF patients, and the like), as well as implantable cardioverter-defibrillator (ICD) variants thereof.

BRIEF DESCRIPTION OF THE DRAWINGS

These and other advantages and features of the present invention will be more readily understood from the following detailed description thereof, when considered in conjunction with the drawings, in which like reference numerals indicate identical structures throughout the several views, and wherein.

DETAILED DESCRIPTION OF THE DRAWINGS

It should be appreciated that while the present invention may be utilized particularly to treat patients suffering congestive heart failure (CHF) and bradycardia. The pacing system of the present invention may also be incorporated into an anti-tachyarrhythmia system including specific high rate pacing and cardioversion shock therapies for providing staged therapies to treat a diagnosed arrhythmia.

Figure 1:
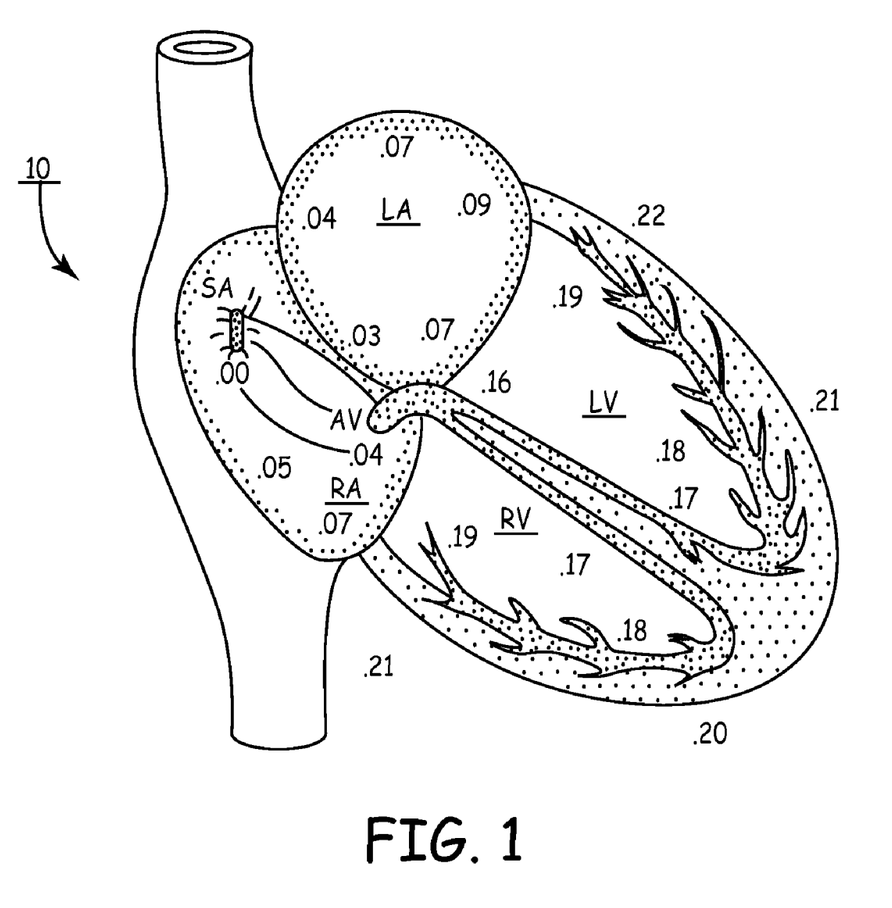
FIG. 1 is an illustration of transmission of the cardiac depolarization waves through the heart in a normal electrical activation sequence.

In FIG. 1, heart 10 includes the upper heart chambers, the right atrium (RA) and left atrium (LA), and the lower heart chambers, the right ventricle (RV) and left ventricle (LV). These vessels provide for blood flow and pumping following depolarization. The sino-atrial node (SA) and atrio-ventricular node (AV), along with the His-Purkinje system comprise the heart's conduction system that transmits electrical signals to trigger the various chambers to contract in a sequential manner.

FIG. 1 is an illustration of transmission of the cardiac depolarization waves through the RA, LA, RV and LV in a normal electrical activation sequence at a normal heart rate with the conduction times exhibited thereon in seconds. The cardiac cycle commences normally with the generation of an electrical impulse at the SA Node in the right atrial wall and its transmission through the atrial conduction pathways of Bachmann's Bundle and the Internodal Tracts from the right atrium into and through the atrial septum to the left atrium. The SA depolarization impulse reaches the Atrio-ventricular (AV) node and the atrial septum within about 40 msec and reaches the furthest walls of the RA and LA within about 70 msec, after which the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent to the RA or LA is also referred to as a sensed P-wave. Although the location and spacing of the external ECG electrodes or implanted unipolar atrial pace/sense electrodes has some influence, the normal P-wave width normally does not exceed 80 msec in width as measured by a high impedance sense amplifier coupled with such electrodes. A normal near field P-wave sensed between closely spaced bipolar pace/sense electrodes and located in or adjacent the RA or the LA usually has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and then travels superiorly though the Purkinje network over the remaining 40 msec. The aggregate RV and LV depolarization wave and the subsequent T-wave signaling repolarization of the depolarized myocardium are referred to as the QRST portion of the PQRST cardiac cycle complex when sensed across external ECG electrodes and displayed. When the amplitude of the QRS ventricular depolarization wave passing access a bipolar or unipolar pace/sense electrode pair located on or adjacent to the RV or LV exceeds a threshold amplitude, it is detected as a sensed R-wave. Although the location and spacing of the external ECG electrodes or implanted unipolar ventricular pace/sense electrodes has some influence, the normal R-wave width is about 80 msec in width as measured by a high impedance sense amplifier. A normal near field R-wave sensed across closely spaced bipolar pace/sense electrodes and located in or adjacent the RV or the LV usually has a width of about 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced CHF and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak-to-peak asynchrony can range from 80 to 200 msec or longer. In RBBB and LBBB patients, the QRS complex is widened far beyond the normal range from >120 msec to 250 msec as measured on surface ECG. This increased width demonstrates the lack of synchrony of the right and left ventricular depolarizations and contractions.

In accordance with one embodiment of the present invention, a method and apparatus is provided to restore the natural depolarization sequence of FIG. 1 to ensure delivery of adequate atrial contribution to stroke volume. Optionally, the present invention may be employed to avoid AVDA sequences and also help maintain synchrony between the right and left ventricular heart chambers so that adequate cardiac output results during delivery of cardiac resynchronization therapy (CRT).

Figure 2:
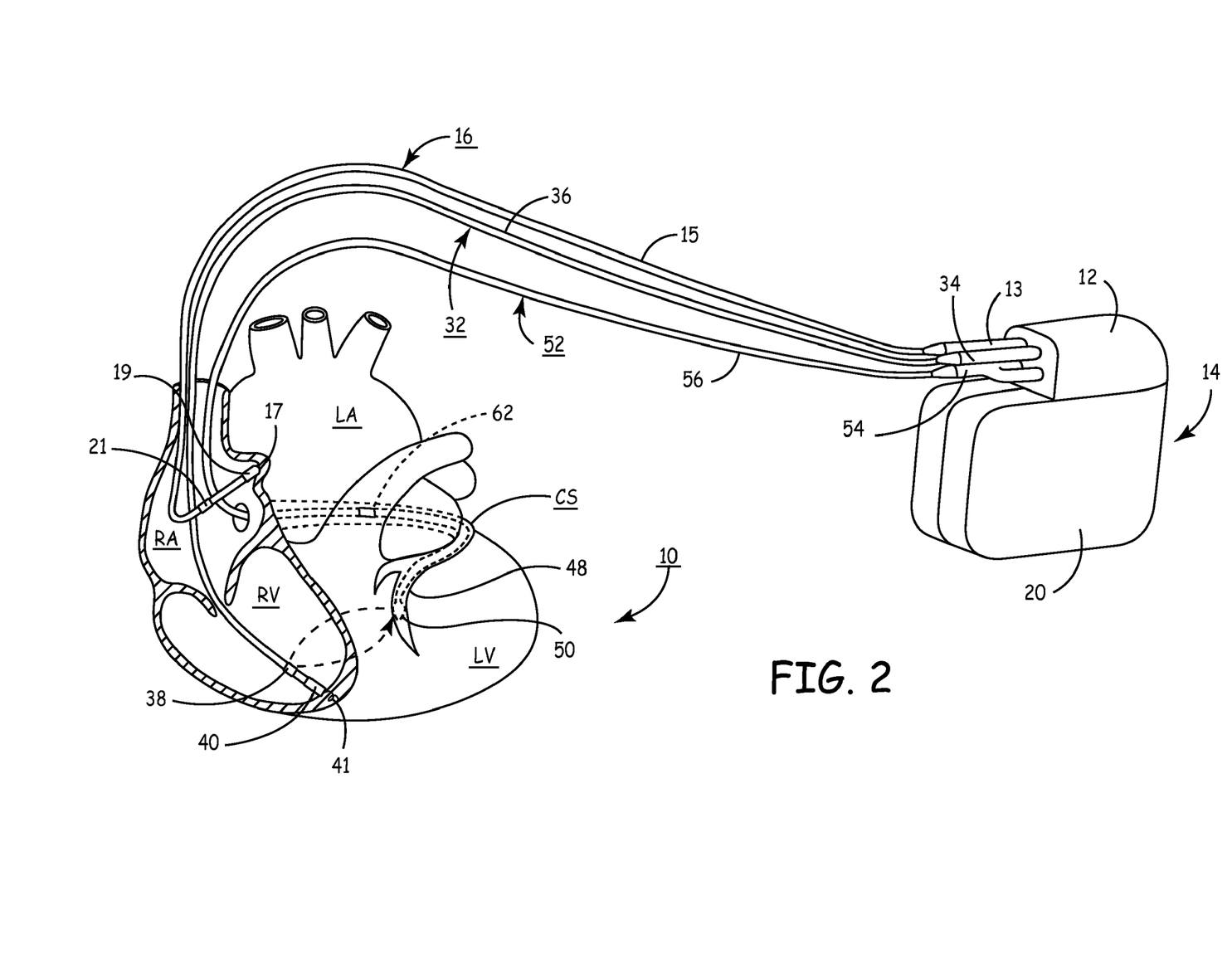
FIG. 2 is a perspective view in partial cross-section with parts removed depicting a three chamber (i.e., atrial and bi-ventricular chamber-based leads) pacing system operatively coupled to the right atrial chamber and both ventricular chambers of a graphically depicted heart.

FIG. 2 is a schematic representation of an implantable three channel cardiac pacemaker of the above noted types for restoring AV synchronous contractions of the atrial and both ventricular chambers with simultaneous biventricular pacing of the right and left ventricles. The IPG 14 is implanted subcutaneously in a patient's body between the skin and the ribs. At least two or, as depicted for a triple-chamber CRT device, three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. For instance, any of the leads may be placed epicardially if desired, or there may be other arrangements made. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV Coronary Sinus (CS) lead 52 is passed through a vein and the RA chamber of the heart 10, into the CS and then inferiorly in a branching vessel of the cardiac vein 48 to extend the distal LV CS pace/sense electrode 50 alongside the LV chamber. The distal end of such LV CS leads is advanced through the superior vena cava, the right atrium, the ostium of the CS, the CS, and into a coronary vein descending from the CS, such as the cardiac vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiorly from the great vein 48.

In accordance with the present invention, the distal, LV CS active pace/sense electrode 50 is paired with the proximal ring RV indifferent pace/sense electrode 38 for delivering LV pace pulses across the bulk of the left ventricle and the intraventricular septum. The distal LV CS active pace/sense electrode 50 is also preferably paired with the distal tip RV active pace/sense electrode 40 for sensing across the RV and LV.

Moreover, in a four-chamber embodiment, LV CS lead 52 could bear a proximal LA CS pace/sense electrode positioned along the lead body to lie in the larger diameter CS adjacent the LA. In that case, the lead body 56 would encase two electrically insulated lead conductors extending proximally from the more proximal LA CS pace/sense electrode(s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

Figure 3A:
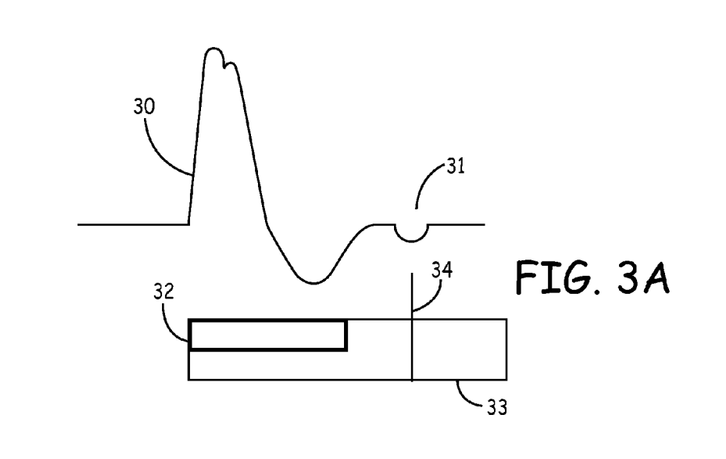
FIG. 3A is a representational schematic drawing of ECG/EGM traces of cardiac activity showing a post-ventricular contraction (PVC) followed by a retrograde atrial event and a PVARP (box) and illustrating a retrograde atrial event occurring during a PVARP.

FIG. 3A is a representational drawing of PVC 30, retrograde atrial event 31, and PVARP 30 to illustrate how retrograde event 31 falls within PVARP 33. The result of this operation is that retrograde atrial event 31 is treated as atrial refractory (AR) sensed event 34. Due to the blanking period 32 (black box), any atrial events occurring during post-ventricular atrial blanking (PVAB) period 32 will not be sensed and any atrial events occurring during post-ventricular atrial refractory period (PVARP) 33 will be treated as non-physiologic atrial refractory events.

PVCs can occur in almost any human being. One issue with PVCs in pacemaker patients is that PVCs can initiate an AVDA sequence with resultant loss of atrial contribution, among other problems. For the past several years, pacemaker manufacturers have extended the PVARP following a PVC so that most retrograde P-waves fall into the PVARP. When this happens, the retrograde P-wave is unable to initiate an AV interval and in a DDD/R or DDI/R pacing mode a ineffectual atrial pacing (AP) stimulus will be delivered when the atria are refractory, and then a ventricular pacing (VP) stimulus will be delivered. If the VP conducts to the atria (i.e., retrograde conduction occurs), then the AVDA sequence can readily persist. So, while extending the PVARP provides an intervention that will, in most cases, prevent the initiation of a pacemaker mediated tachycardia (PMT) but which may initiate a deleterious repetitive AVDA sequence.

Figure 3B:
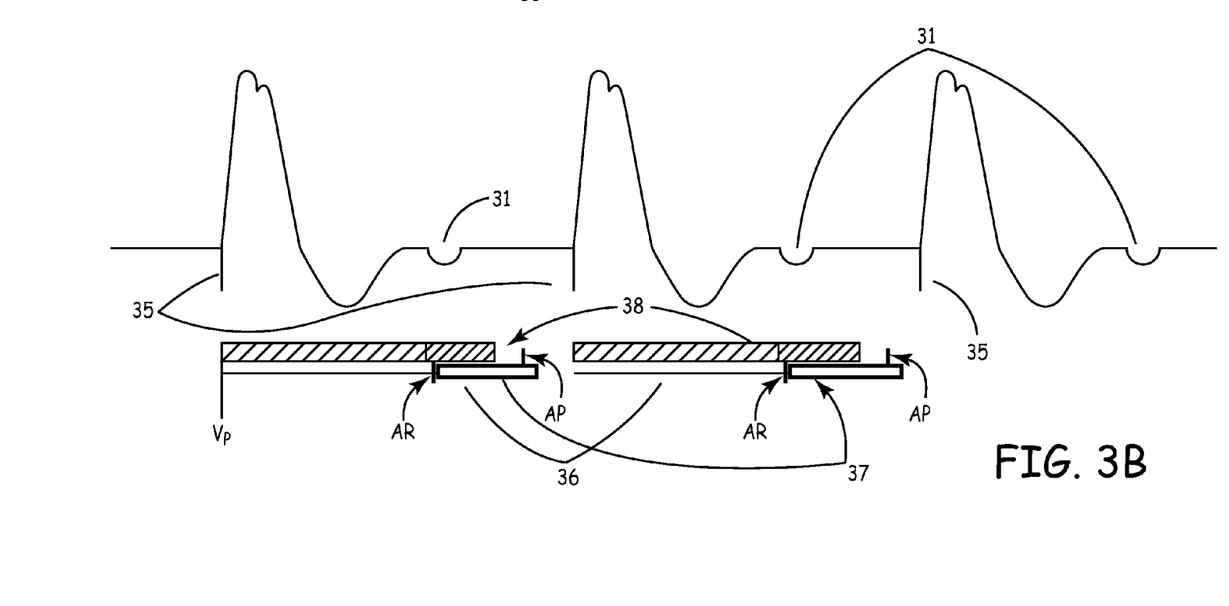
FIG. 3B is a representational schematic drawing of ECG/EGM traces of cardiac activity showing a repetitive pattern of AVDA that can result from when a retrograde atrial event is followed by delivery of an ineffectual atrial pacing stimulus and then a ventricular pacing stimulus.

FIG. 3B schematically illustrates two cardiac cycles following initiation of an AVDA sequence. The reader is cautioned that no particular timing is to be inferred from the size or scale of the elements depicted therein. As depicted, retrograde P-waves 31 occur during the PVARP 38 (at marker line 34 in FIG. 3A). As a result the atrial event is treated as a atrial refractory (AR) event and ineffectual atrial pacing (AP) stimulus is provided while the atria is still refractory (illustrated by bars 36,37) and no paced atrial depolarization occurs. Subsequently, ventricular pacing (VP) stimulus is provided at 35 precipitating another atrial refractory (AR) event (i.e., occurring during PVARP 38). In this way the AVDA sequence can continue for many cardiac cycles during which the pacemaker patient may become symptomatic.

Figure 4:
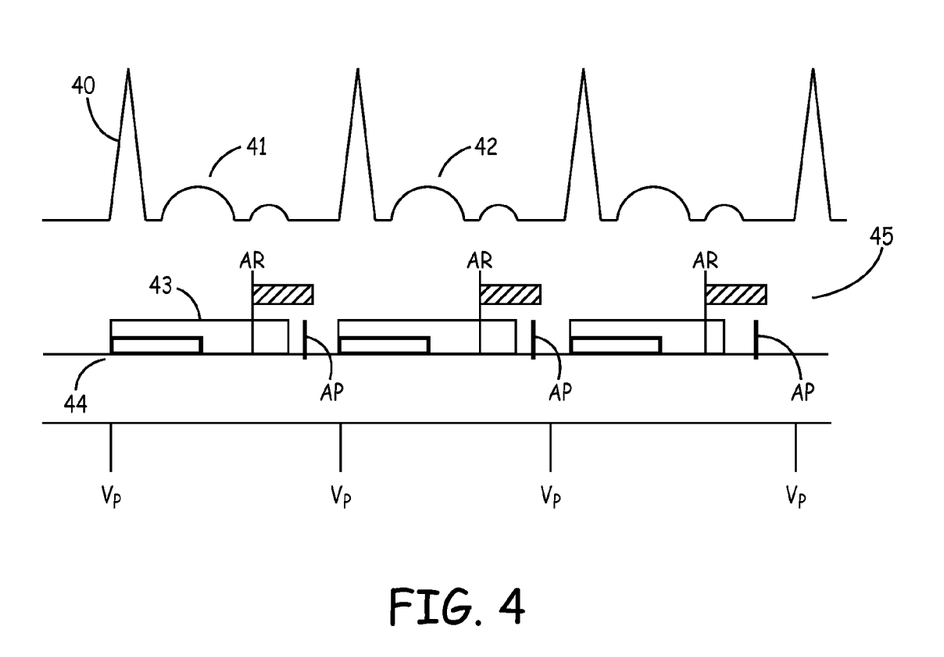
FIG. 4 is a representational schematic drawing of ECG/EGM traces of cardiac activity showing a repetitive pattern of AVDA for four cardiac cycles results when retrograde atrial events are followed by delivery of ineffectual atrial pacing stimulus and then ventricular pacing stimulus.

FIG. 4 depicts an ECG that illustrates how a series of retrograde-conducted atrial refractory (AR) events, closely followed by ineffectual atrial pacing (AP) stimulus can result in persistent AVDA, thereby interrupting a desired pacing modality. Since the retrograde atrial event (AR) event occurs within refractory period of PVARP 43 and pacing stimulus (VP) delivered to the ventricle offers another opportunity for retrograde conduction to the atria thus resulting in another AVDA sequence.

In the event the AVDA does not quickly terminate spurious mode-switching very likely will begin. To avoid the disadvantageous hemodynamic effects of persistent AVDA sequences, the inventors propose that the delivered atrial pacing (AP) energy be increased. Thus, even if the timing is not changed, the increased energy delivered to the atrial chamber(s) is more likely to result in atrial capture. For example, if the amplitude and/or pulse width of the atrial pacing (AP) stimulus is increased and still delivered during the relative refractory period of the chamber(s), the AP may nevertheless result in atrial capture. In addition or in lieu of increasing the AP energy, a dedicated AVDA mode-switch may be performed (e.g., from a sensor-based pacing rate to a non-sensor-based pacing modality like DDD or DDI having fixed intervals and beginning at or near the last sensor-based rate).

In one embodiment of the above-mentioned means for terminating an AVDA sequence, a series of different AP stimulus may be provided depending on the then-present AR-AP intervals. For example, on a beat-to-beat or several beat basis, the AR-AP intervals are measured, stored and/or utilized to set AP stimulus energy level. In this embodiment, if the AR-AP interval is greater than about 400 ms then provide the AP stimulus at the pre-existing (or pre-programmed) level. If the AR-AP interval is greater than about 300 ms and less than about 400 ms then provide the AP stimulus at some increment (e.g., one volt) above the pre-existing (or pre-programmed) level. In this case for example, the AP stimulus may be increased from about three volts (3V) to about four volts (4V). In the event that the AR-AP interval is less than about 300 ms then provide the AP stimulus at about five volts (5V) or the pre-programmed maximum level.

Of course, as recognized by those of skill in the art the foregoing methods may be implemented in a processor-based apparatus on a computer-readable medium containing instructions for performing the various steps thereof. Other aspects of the present invention also will be readily appreciated by those of skill in the art; for example, one or more look up tables (LUT) may be used to store more than three alternate AP stimulus energy levels for the dynamic termination of an AVDA sequence. Temporal recordings of the pace/sense history for a given patient may be stored and read out by a remote programmer and/or provided to remote equipment via telemetry and the like. In addition, a patient notification scheme may be used to alert the patient, a clinician or a care provider that a deleterious AVDA sequence is occurring (or has recently occurred). The patient notification scheme may include tactile, visual and/or audible cues and may be portable or not. In the event that processor speeds and energy requirements are improved from the present day, the present invention may optimally provided beat-to-beat detection of a first AVDA sequence with immediate termination provided (e.g., mode switching, increased-energy atrial pacing stimulus, etc.).

The preceding specific embodiments are illustrative of the practice of the invention. It is to be understood, therefore, that other expedients known to those of skill in the art or disclosed herein may be employed without departing from the invention or the scope of the appended claims. It is therefore to be understood that the invention may be practiced otherwise than is specifically described, without departing from the scope of the present invention. As to every element, it may be replaced by any one of infinite equivalent alternatives, only some of which are disclosed in the specification. For example, the methods provided by the present invention may be implemented in a combination of hardware, software and/or firmware on a general purpose computer platform, a microprocessor-based platform or using a combination of RAM, ROM, EEPROM circuits and the like as is well known in the art. In the events the methods are thus performed instructions for performing said methods may be stored on a computer readable medium and executed as described and claimed herein.

We claim:

1. A method of detecting and terminating an AV Desynchronization Arrhythmia (AVDA) sequence in a patient having a dual chamber pacemaker pulse generator including atrial and ventricular pacing and sensing electrodes said electrodes being for delivering electrical pulses from said generator for pacing and sensing depolarization events and non-physiologic events of the heart of the patient, said pacing having mode-switching capability and adjustable pacing pulse energies wherein said method comprises the steps of:
   sensing a premature ventricular contraction event or a other ventricular event, wherein said event is not closely preceded by an atrial depolarization;
   sensing a retrograde atrial refractory sensed event before a scheduled atrial pacing stimulus is delivered; and
   triggering an increased energy atrial pace stimulation signal to a portion of an atrium of a patient at the time the scheduled atrial pacing stimulus is delivered.

2. A method according to claim 1, wherein the AVDA sequence comprises a repeating pattern.

3. A method according to claim 2, wherein said repeating pattern comprises at least three cardiac events, said at least three cardiac events comprising:
   an atrial refractory (AR) sensed event occurring soon after the ventricular pace (VP) stimulation event;
   an ineffectual atrial pace (AP) stimulation event delivered during an absolute or relative refractory period of an atrial chamber, said stimulation deemed ineffectual due to the atrial refractory (AR) sensed event; and
   a ventricular pace stimulation event.

4. A method according to claim 3, further comprising the steps of preventing continuation of the detected AVDA sequence by performing at least one of the following steps:
   increasing the energy delivered for at least one subsequent atrial pace stimulation event based at least in part on the magnitude of the temporal interval between the atrial refractory (AR) sensed event and the scheduled atrial pace (AP) stimulation event,
   lengthening an atrial escape interval for at least one cycle following a premature ventricular depolarization, or
   extending a first non-competitive atrial pacing (NCAP) interval.

5. A method according to claim 4, wherein said increasing step is performed by increasing the electrical potential, electrical current and/or pulse width of the atrial pace stimulation signal.

6. A method according to claim 5, wherein said increasing step is performed in a staged termination scheme, wherein said increasing step varies in steps between a minimum or pre-existing level and a maximum level.

7. A method according to claim 4, further comprising the step of reducing the energy delivered for subsequent atrial pace stimulation events to approximately the magnitude of said energy before said AVDA sequence was detected.

8. A method according to claim 3, further comprising the step of:
   increasing a delay interval following the atrial refractory sensed event so that no atrial pace (AP) stimulation event occurs during said increased delay interval; and
   delaying delivery of the ventricular pacing (VP) stimulus from a pre-programmed moment.

9. A method according to claim 8, wherein said delay is increased from a prior value to a value of approximately 400 milliseconds.

10. A method of performing adaptive atrial pacing during antibradycardia DDD/R operation of an implantable medical device in order to avoid atrial non-capture following intrinsic, non-physiologic atrial depolarizations, comprising the steps of:
   determining if an atrial pace stimulus is scheduled to occur following a closely-coupled, refractory, retrograde atrial depolarization; and
   delivering a relatively higher energy output atrial pace stimulus for at least a one of:
   a present cardiac cycle,
   a subsequent cardiac cycle, or
   at least one subsequent atrial pace stimulus event.

11. A method according to claim 10, wherein said delivering step further comprises the step of:
   increasing the energy delivered for the at least one subsequent atrial pace (AP) stimulus event.

12. A method according to claim 11, wherein said increasing step is performed by increasing an electrical potential and/or an electrical current of the atrial pace stimulus.

13. A method according to claim 11, wherein said increasing step is performed by increasing the pulse width of the atrial pace stimulus.

14. A method of detecting an AV Desynchronization Arrhythmia (AVDA) sequence in a patient having a dual chamber pacemaker pulse generator including atrial and ventricular pacing and sensing electrodes said electrodes being for delivering electrical pulses from said generator for pacing and sensing depolarization events and non-physiologic events of the heart of the patient, said pacing having mode-switching capability and adjustable pacing pulse energies wherein said method comprises the steps of:
- a) sensing a premature ventricular contraction event, wherein said premature ventricular contraction event is not closely preceded by an atrial depolarization;
- b) sensing a retrograde atrial refractory-sensed event;
- c) triggering delivery of an atrial pace stimulus signal to a portion of an atrium of the patient during a relative refractory period of the atrium following the occurrence of the retrograde atrial refractory-sensed event; and
- d) confirming that the triggered atrial pace stimulus captured an atrial chamber.

15. A method according to claim 14, wherein the detected AVDA sequence comprises a repeating pattern, and further comprising performing step of: e) performing steps a) through d) for at least three cardiac cycles.

16. A method according to claim 15, wherein each of said at least three cardiac cycles of the repeating pattern comprises:
- a retrograde atrial refractory-sensed (AR) event precipitated by a ventricular pace (VP) stimulus event;
- an atrial pace (AP) stimulus event delivered during a refractory period caused by said retrograde atrial refractory-sensed (AR) event; and
- a ventricular pace (VP) stimulus event.

17. A method according to claim 14, further comprising the steps of preventing continuation of the detected AVDA sequence by performing the following step: increasing the energy delivered for at least one subsequent atrial pace (AP) stimulation event.

18. A method according to claim 17, wherein said increasing step is performed by increasing magnitude of an electrical potential of the atrial pace (AP) stimulus.

19. A method according to claim 17, wherein said increasing step is performed by increasing the pulse width of the atrial pace (AP) stimulus.

20. A method according to claim 17, further comprising the step of reducing the energy delivered for subsequent atrial pace stimulus events to approximately the magnitude of said energy before said AVDA sequence was detected.

21. A method according to claim 3, further comprising the step of increasing a delay interval following the atrial refractory sensed event so that no pace stimulation event occurs during said increased delay interval.

22. A method according to claim 21, wherein said delay is increased from a prior value to a value of approximately 400 milliseconds.

23. A dual chamber pacemaker implantable pulse generator for attachment with atrial and ventricular pacing and sensing electrodes said electrodes being for delivering electrical pulses from said generator for pacing and sensing depolarization of a patient's heart in the atrium and the ventricle respectively, said being at adjustable atrial pacing pulse energies, said generator comprising:
- atrial sensing means adapted to be coupled through an atrial sense electrode for generating a atrial refractory-sensed (AR) event signal in response to a retrograde-conducted ventricular depolarization;
- atrial loss-of-capture means for determining if a pacing stimulus delivered subsequent to the generation of the atrial refractory-sensed (AR) event signal fails to capture an atrial chamber and providing a loss-of-capture signal; and
- a pulse generator means for generating a series of atrial pacing stimuli at a first energy level during nominal operation and for providing a second energy level, greater than said first energy level, in response to receipt of the loss-of-capture signal.

24. A computer-readable medium for storing instructions for performing the following method in conjunction with a processor-based apparatus, comprising:
- instructions for sensing a ventricular contraction event, wherein said ventricular contraction event is not closely preceded by an atrial depolarization;
- instructions for sensing a retrograde atrial refractory-sensed event precipitated by said ventricular contraction event; and
- instructions for triggering delivery of an atrial pace stimulus signal during a relative refractory period of the atrium following the occurrence of the retrograde atrial refractory-sensed event.

* * * * *